(12) United States Patent
Jia

(10) Patent No.: US 9,999,733 B2
(45) Date of Patent: Jun. 19, 2018

(54) SAFETY SYRINGE

(71) Applicant: Jian-Yu Jia, Yuhuan (CN)

(72) Inventor: Jian-Yu Jia, Yuhuan (CN)

(*) Notice: Subject to any disclaimer, the term of this patent is extended or adjusted under 35 U.S.C. 154(b) by 132 days.

(21) Appl. No.: 15/293,991

(22) Filed: Oct. 14, 2016

(65) Prior Publication Data

US 2018/0028758 A1 Feb. 1, 2018

(30) Foreign Application Priority Data

Jul. 26, 2016 (CN) .......................... 2016 1 0600955

(51) Int. Cl.
*A61M 5/32* (2006.01)
*A61M 5/315* (2006.01)
*A61M 5/34* (2006.01)
*A61M 5/31* (2006.01)

(52) U.S. Cl.
CPC ...... *A61M 5/31566* (2013.01); *A61M 5/3135* (2013.01); *A61M 5/31513* (2013.01); *A61M 5/31576* (2013.01); *A61M 5/345* (2013.01)

(58) Field of Classification Search
CPC .... A61M 5/3134; A61M 5/344; A61M 5/345; A61M 5/322; A61M 2005/323
See application file for complete search history.

(56) References Cited

U.S. PATENT DOCUMENTS 8,562,561 B2 10/2013 Chang
9,155,845 B2 10/2015 Thayer

FOREIGN PATENT DOCUMENTS

| CN | 100443130 C | 12/2008 |
|---|---|---|
| CN | 201290969 Y | 8/2009 |
| CN | 103330976 B | 5/2015 |
| JP | 2008525059 A | 7/2008 |
| JP | 2012086057 A | 5/2012 |

*Primary Examiner* — Deanna K Hall
(74) *Attorney, Agent, or Firm* — Locke Lord LLP; Tim Tingkang Xia, Esq.

(57) ABSTRACT

The safety syringe includes a barrel having a clamping slot, a large sealing ring and a zero line; a plunger having a pull pawl and an annular convex clamping disc, an avoiding seams; a rubber plug; a needle connector having annular clamping pawls, an inner sealing ring and a pullback ring; and a locking body made of a polymer material with elasticity and having a sealing disc, a sealing ring, a clamping ring and a checking ring. The sealing disc, large sealing ring, sealing ring and inner sealing ring are engaged to constitute a sealing structure. When the clamping ring meshed with the pull pawl is dragged to retract inwards, the sealing ring and pullback ring are engaged to pull the needle connector to retract, and the checking ring is plugged into the inner cavity of the clamping pawls to fix the clamping pawls in the clamping slot.

17 Claims, 13 Drawing Sheets

SAFETY SYRINGE

CROSS-REFERENCE TO RELATED PATENT APPLICATION

This application claims priority to and the benefit of Chinese Patent Application No. CN201610600955.X, filed Jul. 26, 2016 in the State Intellectual Property Office of P.R. China, which is incorporated herein in its entirety by reference.

FIELD OF THE INVENTION

This invention relates generally to medical instruments, and more particularly, to a safety syringe.

BACKGROUND OF THE INVENTION

The background description provided herein is for the purpose of generally presenting the context of the present invention. The subject matter discussed in the background of the invention section should not be assumed to be prior art merely as a result of its mention in the background of the invention section. Similarly, a problem mentioned in the background of the invention section or associated with the subject matter of the background of the invention section should not be assumed to have been previously recognized in the prior art. The subject matter in the background of the invention section merely represents different approaches, which in and of themselves may also be inventions.

A syringe is the most frequently used medical instrument clinically. The most common syringe used at present is a disposable syringe made of plastic. Although, the disposable syringe has effectively controlled the problems of cross infection, along with the progress of technologies, a one-way protection concept falls behind. A syringe needle polluted by patient's blood in a use process may harm a user, and the discarded syringes also may accidentally harm those people in a subsequent storage, transportation and destroying process. Besides, the existing disposable syringe has the defects of reuse if kept intactly, exposure of the syringe needle after injection due to no safety apparatus, etc. Thus, lawbreakers can reuse the used discarded disposable syringes without disinfection, leading to great probability in virus propagation and cross infection. Therefore, a multi-way protection concept occurs along with the trend. The safety syringe is a medical instrument in the multi-way protection concept, and it not only protects a patient from cross infection, but also protects medical staff using it and personnel who may contact it subsequently from the harm of the syringe needle.

Currently, there are many products and patents of retractable safety syringes available, for example, CN 100443130C, CN 103330976B, U.S. Pat. No. 9,155,845, U.S. Pat. No. 8,562,561, JP2008-525059, and JP2012-086057. Some of them have complicated structures, especially, some of them have more than seven parts, cannot be produced in batch and are high in production cost; some of them cannot use a standard injection needle or cannot exchange the needle; some of them use an O-shaped ring to solve an airtightness problem of a cylinder, but the O-shaped ring is small in size and is difficult in implementation of mechanical assembly; some of them cannot inject for many times, the safety apparatus is activated when a plunger is pushed to the bottom and most of them are not equipped with a function of selectively activating the safety mechanism.

Article 3.1 of International Standards ISO7886-4 *Sterile hypodermic syringes for single use-Part 4: Syringues with reuse prevention feature* puts forth requirements of selectively activating the safety mechanism by a user himself/herself.

Chinese Patent Application No. CN200820200380.3 (i.e., Publication No. CN201290969Y) discloses a self-destruction safety syringe, it comprises a cylinder, a push rod, a piston, a connector and a needle holder, where a clamping position is disposed between the connector and the cylinder, an elastic clamping slot is disposed in a connector inner hole and the top end of the push rod is provided with an auxiliary rotating device capable of rotating the connector along with the push rod. A self-destruction process of the self-destruction safety syringe is as follows: after injection, the pull rod pulls needle holder back into the cylinder by slightly pressing the push rod and matching clamping device, then the push rod is broken along a breaking recess in the push rod and is placed back into a recycling box. The self-destruction safety syringe can be self-destroyed after use, but the self-destruction can be guaranteed as long as an operator breaks the push rod, it is troublesome to operate, and has demand on a breaking force applied to the push rod, and the push rod cannot be broken in case of not enough force.

Therefore, a heretofore unaddressed need exists in the art to address the aforementioned deficiencies and inadequacies.

SUMMARY OF THE INVENTION

One of the objectives of this invention is a selectively activated and non-reusable safety syringe to solve the above-noted technical problems, which achieves the following effects:

Only five components are used. Thus, the syringe is simple in structure, low in cost and capable of realizing mechanical batch production.

The syringe uses a standard needle. The needle is exchangeable.

Air exhaustion can be implemented to a zero line. Therefore, the syringe can be used for multiple injections. The safety mechanism is activated after the syringe needle is pulled out of a body, thereby completely realizing a selection over activating time of the safety mechanism by a user himself/herself.

The polluted needle can be retracted back into the cylinder for shielding. The shielded plunger and the cylinder can realize a limiting action, the plunger is avoided being pushed out of the cylinder and the needle puncture harm is solved.

The syringe has only five components, which ensure not only to firm fixing of the needle, but also to be sealed without leakage, and meanwhile, the user can select the activating time of the safety mechanism.

In one aspect of the invention, a safety syringe comprises an annular hollow barrel, a plunger capable of sliding in the barrel, a rubber plug mounted on the plunger, a slidable needle connector mounted at the front end of the barrel, a locking body capable of clamping a needle connector on the barrel and forming a sealing structure together with the barrel and needle connector, wherein the locking body can also be meshed with the plunger and then dragged back into the barrel by the plunger. The locking body is made of a polymer material with elasticity, the barrel is provided with a clamping slot, a large sealing ring and a zero line, and the inner side of the back end of the barrel has an annular concave clamping slot; the front end of the plunger is provided with a pull pawl and an annular convex clamping disc, the plunger has avoiding seams adjacent to a clamping disc, the outer diameter of the clamping disc is smaller than inner diameter of the clamping slot at the barrel, the clamping disc has elasticity and is located in the clamping slot when being pushed to be deformed by the plunger; the needle connector is provided with annular clamping pawls, an inner sealing ring and a pullback ring; the locking body is provided with a sealing disc, a sealing ring, a clamping ring and a checking ring, the sealing disc and the large sealing ring of the barrel are matched to constitute a sealing structure A, the sealing ring and the inner sealing ring of the needle connector are matched to constitute a sealing structure B, the sealing ring and the pullback ring of the needle connector are matched to pull the needle connector to retract, the clamping ring and the pull pawl of the plunger are meshed to be dragged by the plunger to retract inwards, and the checking ring can be plugged into the inner cavity of the clamping pawls of the needle connector to fix the clamping pawls in the clamping slot of the barrel.

In one embodiment, the inner side of the barrel has a front convex ring and a back convex ring which are annularly convex, the front convex ring and the back convex ring are axially arranged along the barrel and the clamping slot is formed between the front convex ring and the back convex ring.

In one embodiment, the clamping disc comprises a front clamping disc and a back clamping disc, which are axially arranged along the plunger, the outer diameters of the front clamping disc and the back clamping disc are both larger than the inner diameters of the front convex ring and the back convex ring, and the avoiding seams are adjacent to the back clamping disc.

In one embodiment, the section of the plunger along its radial direction is cross-shaped, each side of the plunger has one avoiding seam, and the lower surface of the back clamping disc is provided with a folded line slot.

In one embodiment, each side of the plunger is provided with a breaking port for breaking the plunger.

In one embodiment, when the zero line of the barrel and a front sealing line of the rubber plug are coincided, a gap with an activating displacement L is reserved between the front end surface of the front clamping disc of the plunger and the bottom end surface of the rubber plug; another gap with an activating displacement L is reserved between the bottom end surface of the pull pawl of the plunger and the front end surface of the clamping ring.

In one embodiment, the clamping slot of the barrel is an annular groove and can be meshed with the annular clamping pawls of the needle connector, and after the checking ring of the locking body is plugged into the inner cavity of the annular clamping pawls, the needle connector can be firmly fixed on the barrel; and after the checking ring of the locking body is moved from the inner cavity of the annular clamping pawls, the annular clamping pawls can be folded so as to smoothly enter the inner cavity of the barrel.

In one embodiment, the large sealing ring of the barrel and the sealing disc of the locking body constitute the sealing structure A by interference fit, and the sealing ring at the front end of the locking body and the inner sealing ring of the needle connector are matched to constitute the sealing structure B.

In one embodiment, the pull pawl of the plunger can be opened and closed, when opened, the outer diameter of the pull pawl is larger than the inner diameter of the clamping ring of the locking body, and after penetrating through the clamping ring, the pull pawl is opened to be clamped on the front end surface of the clamping ring; at this point, the plunger can drag the locking body to move into the barrel.

In one embodiment, two or more activating ribs are uniformly distributed on the front end surface of the front clamping disc of the plunger and the height of the activating ribs is equal to the reserved activating displacement L; and when the plunger moves forward, the activating ribs can support the bottom end surface of the rubber plug to inject.

In one embodiment, the sectional shape of the activating ribs can be round, rectangular or triangular.

In one embodiment, a projection total area of the activating ribs on the front clamping disc is smaller than the area of the front clamping disc.

In one embodiment, the activating ribs can move to the bottom end surface of the rubber plug when the plunger is subjected to an axial activating force and is wedged into the rubber plug to move by certain displacement L, the pull pawl penetrates through the clamping ring of the locking body and is then opened to be clamped on the front end surface of the clamping ring, at this point, the plunger and the locking body are clamped into a whole completely, and the safety mechanism of the safety syringe is activated.

In one embodiment, the annular clamping pawls of the needle connector are radially uniformly distributed and have a number of more than two.

According to the invention, since the annular clamping pawls on the needle connector are meshed with the clamping slot at the front end of the barrel, when the checking ring of the locking body is plugged into the inner cavity of the clamping pawls, the clamping pawls are jacked to not retract to the center, and the needle connector is firmly fixed on the barrel. The large sealing ring of the barrel and the sealing disc of the locking body constitute the sealing structure A by interference fit, and the sealing ring at the front end of the locking body and the inner sealing ring of the needle connector are matched to constitute the sealing structure B, and these two sealing structures can solve the airtightness problem of the barrel such that the syringe is not leaked in use. Since the locking body achieves the three actions of fixing the needle connector, constituting the two sealing structures A and B and dragging to retract the needle connector, and one part has three actions, thus reducing the number of parts. When the plunger drags the rubber plug till the front sealing line of the rubber plug and the zero line of the barrel are coincided, it means that liquid in the barrel is totally injected, at this point, the pull pawl of the plunger is away from the front end of the clamping ring of the locking body by a distance L, the plunger and the locking body are not locked into a whole yet, the locking body is impossible to be hooked to retract, and the syringe cannot be failed due to retracting of the plunger and can finish operations such as air exhausting and multi-injection and the like. When deciding not to use the syringe any more after reinjection, medical staff can apply a force to the plunger in the axial direction, the activating ribs on the front clamping disc of the plunger will be wedged into the rubber plug and move forward by the distance L, then the pull pawl of the plunger penetrates through the clamping ring of the locking body to reach the front end surface of the clamping ring, since the outer diameter of the pull pawl is larger than the inner diameter of the clamping ring of the locking body, the pull pawl connects the plunger and the locking body into a whole to retract the plunger back into the barrel, the plunger drives the locking body to also retract into the barrel to relieve the constraint to the clamping pawls of the needle connector, the plunger is continued to pull to retract the locking body continuously, when the sealing ring of the locking body hooks the pullback ring of the needle connector, the needle connector without constraint is also pulled into the barrel, the needle connected to the needle connector is pulled back into the barrel to be shielded, and thus the needle polluted by patient's blood will not cause harm; the plunger is fixed in the barrel by arranging the clamping slot and the clamping disc, the needle on the needle connector is fixed in the barrel to realize a limiting action of the plunger, and the needle is avoided releasing from the barrel in a transportation process to cause harm to outside.

The requirements of the International Standards IS07886-4 on the safety mechanism of the selectively activated safety syringe as well as the shielding requirement on the polluted needle are all realized.

These and other aspects of the present invention will become apparent from the following description of the preferred embodiment taken in conjunction with the following drawings, although variations and modifications therein may be affected without departing from the spirit and scope of the novel concepts of the disclosure.

BRIEF DESCRIPTION OF THE DRAWINGS

The accompanying drawings illustrate one or more embodiments of the present invention and, together with the written description, serve to explain the principles of the invention. Wherever possible, the same reference numbers are used throughout the drawings to refer to the same or like elements of an embodiment.

Figure 1:
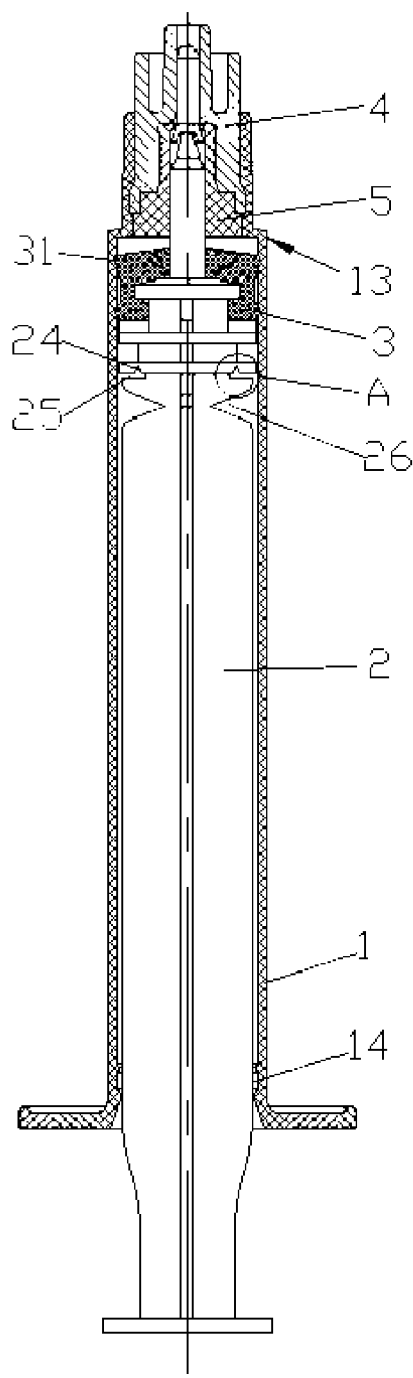
FIG. 1 is a state diagram that a syringe is not used after assembly according to one embodiment of the present invention.
Figure 2:
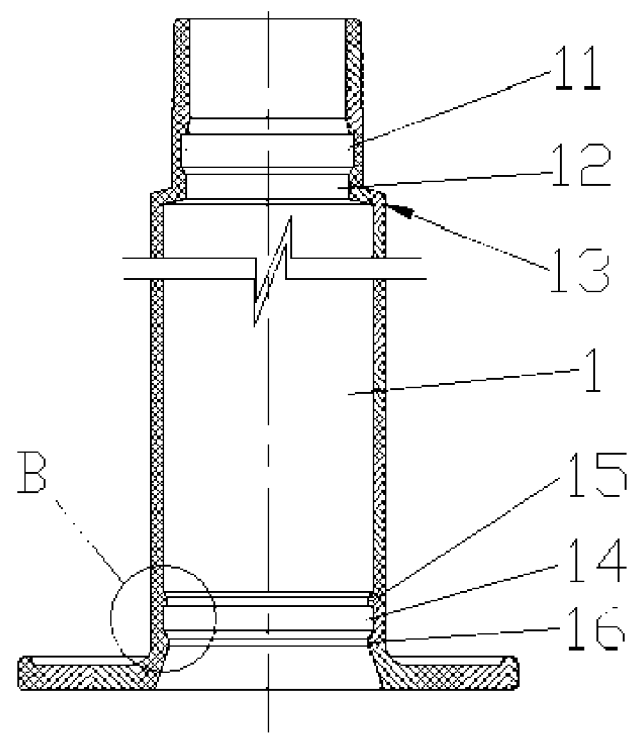
FIG. 2 is a sectional view of a barrel according to one embodiment of the present invention.

The following lists reference numerals and their corresponding components in the drawings:

1—hollow barrel; 11—clamping slot; 12—large sealing ring; 13—zero line; 14—clamping slot; 15—front convex ring; 16—back convex ring; 17—clamping surface; 18—guiding surface; 19—guiding in surface;

2—plunger; 21—pull pawl; 22—front clamping disc; 221—front end surface; 222—activating rib; 23—back clamping disc; 24—avoiding seam; 25—folded line slot; 26—breaking port;

3—rubber plug; 31—front sealing line; 32—bottom end surface;

4—needle connector; 41—annular clamping pawl; 411—inner cavity; 42—inner sealing ring; 43—pullback ring;

5—locking body; 51—sealing disc; 52—sealing ring; 53—clamping ring; 531—front end surface; and 54—checking ring.

DETAILED DESCRIPTION OF THE INVENTION

The present invention will now be described more fully hereinafter with reference to the accompanying drawings, in which exemplary embodiments of the present invention are shown. The present invention may, however, be embodied in many different forms and should not be construed as limited to the embodiments set forth herein. Rather, these embodiments are provided so that this disclosure will be thorough and complete, and will fully convey the scope of the invention to those skilled in the art. Like reference numerals refer to like elements throughout.

The terms used in this specification generally have their ordinary meanings in the art, within the context of the invention, and in the specific context where each term is used. Certain terms that are used to describe the invention are discussed below, or elsewhere in the specification, to provide additional guidance to the practitioner regarding the description of the invention. For convenience, certain terms may be highlighted, for example using italics and/or quotation marks. The use of highlighting and/or capital letters has no influence on the scope and meaning of a term; the scope and meaning of a term are the same, in the same context, whether or not it is highlighted and/or in capital letters. It will be appreciated that the same thing can be said in more than one way. Consequently, alternative language and synonyms may be used for any one or more of the terms discussed herein, nor is any special significance to be placed upon whether or not a term is elaborated or discussed herein. Synonyms for certain terms are provided. A recital of one or more synonyms does not exclude the use of other synonyms. The use of examples anywhere in this specification, including examples of any terms discussed herein, is illustrative only and in no way limits the scope and meaning of the invention or of any exemplified term. Likewise, the invention is not limited to various embodiments given in this specification.

It will be understood that when an element is referred to as being "on" another element, it can be directly on the other element or intervening elements may be present therebetween. In contrast, when an element is referred to as being "directly on" another element, there are no intervening elements present. As used herein, the term "and/or" includes any and all combinations of one or more of the associated listed items.

It will be understood that, although the terms first, second, third, etc. may be used herein to describe various elements, components, regions, layers and/or sections, these elements, components, regions, layers and/or sections should not be limited by these terms. These terms are only used to distinguish one element, component, region, layer or section from another element, component, region, layer or section. Thus, a first element, component, region, layer or section discussed below can be termed a second element, component, region, layer or section without departing from the teachings of the present invention.

It will be understood that when an element is referred to as being "on," "attached" to, "connected" to, "coupled" with, "contacting," etc., another element, it can be directly on, attached to, connected to, coupled with or contacting the other element or intervening elements may also be present. In contrast, when an element is referred to as being, for example, "directly on," "directly attached" to, "directly connected" to, "directly coupled" with or "directly contacting" another element, there are no intervening elements present. It will also be appreciated by those of skill in the art that references to a structure or feature that is disposed "adjacent" to another feature may have portions that overlap or underlie the adjacent feature.

The terminology used herein is for the purpose of describing particular embodiments only and is not intended to be limiting of the invention. As used herein, the singular forms "a," "an," and "the" are intended to include the plural forms as well, unless the context clearly indicates otherwise. It will be further understood that the terms "comprises" and/or "comprising," or "includes" and/or "including" or "has" and/or "having" when used in this specification specify the presence of stated features, regions, integers, steps, operations, elements, and/or components, but do not preclude the presence or addition of one or more other features, regions, integers, steps, operations, elements, components, and/or groups thereof.

Furthermore, relative terms, such as "lower" or "bottom" and "upper" or "top," may be used herein to describe one element's relationship to another element as illustrated in the figures. It will be understood that relative terms are intended to encompass different orientations of the device in addition to the orientation shown in the figures. For example, if the device in one of the figures is turned over, elements described as being on the "lower" side of other elements would then be oriented on the "upper" sides of the other elements. The exemplary term "lower" can, therefore, encompass both an orientation of lower and upper, depending on the particular orientation of the figure. Similarly, if the device in one of the figures is turned over, elements described as "below" or "beneath" other elements would then be oriented "above" the other elements. The exemplary terms "below" or "beneath" can, therefore, encompass both an orientation of above and below.

Unless otherwise defined, all terms (including technical and scientific terms) used herein have the same meaning as commonly understood by one of ordinary skill in the art to which the present invention belongs. It will be further understood that terms, such as those defined in commonly used dictionaries, should be interpreted as having a meaning that is consistent with their meaning in the context of the relevant art and the present disclosure, and will not be interpreted in an idealized or overly formal sense unless expressly so defined herein.

As used herein, "around," "about," "substantially" or "approximately" shall generally mean within 20 percent, preferably within 10 percent, and more preferably within 5 percent of a given value or range. Numerical quantities given herein are approximate, meaning that the terms "around," "about," "substantially" or "approximately" can be inferred if not expressly stated.

As used herein, the terms "comprise" or "comprising," "include" or "including," "carry" or "carrying," "has/have" or "having," "contain" or "containing," "involve" or "involving" and the like are to be understood to be open-ended, i.e., to mean including but not limited to.

As used herein, the phrase "at least one of A, B, and C" should be construed to mean a logical (A or B or C), using a non-exclusive logical OR. It should be understood that one or more steps within a method may be executed in different order (or concurrently) without altering the principles of the invention.

The description is now made as to the embodiments of the present invention in conjunction with the accompanying drawings. In accordance with the purposes of the present invention, as embodied and broadly described herein, the present invention relates to a safety syringe.

Embodiments of the Safety Syringe

Referring to FIG. 1, a selectively activated retractable safety syringe is shown according to one embodiment of the invention. The selectively activated retractable safety syringe comprises an annular hollow barrel 1, a plunger 2 capable of sliding in the barrel 1, a rubber plug 3 mounted on the plunger 2, a slidable needle connector 4 mounted at the front end of the barrel 1, a locking body 5 capable of clamping a needle connector 4 on the barrel 1 and forming a sealing structure together with the barrel 1 and needle connector 4, wherein the locking body 5 is meshed with the plunger 2 and then dragged back into the barrel 1 by the plunger 2 and the locking body 5 is made of a polymer material with elasticity.

Referring to FIGS. 1-6, the front end of the barrel 1 is provided with a clamping slot 11, a large sealing ring 12 and a zero line 13, and the inner side of the back end of the barrel 1 has an annular concave clamping slot 14; the front end of the plunger 2 is provided with a pull pawl 21 and an annular convex clamping disc, the plunger 2 has avoiding seams 24 adjacent to a clamping disc, the outer diameter of the clamping disc is smaller than inner diameter of the clamping slot 14 of the barrel 1, the clamping disc has elasticity and is located in the clamping slot 14 when being pushed to be deformed by the plunger 2; the needle connector 4 is provided with annular clamping pawls 41, an inner sealing ring 42 and a pullback ring 43; the locking body 5 is provided with a sealing disc 51, a sealing ring 52, a clamping ring 53 and a checking ring 54, the sealing disc 51 and the large sealing ring 12 of the barrel 1 are matched to constitute a sealing structure A, the sealing ring 52 and the inner sealing ring 42 of the needle connector are matched to constitute a sealing structure B, the sealing ring 52 and the pullback ring of the needle connector 43 are matched to pull the needle connector 4 to retract, the clamping ring 53 and the pull pawl 21 of the plunger 2 are meshed to be dragged by the plunger to retract inwards, and the checking ring 54 can be plugged into the inner cavity 411 of the clamping pawls 41 of the needle connector 4 to fix the clamping pawls 41 in the clamping slot 11 of the barrel 1.

Figure 6:
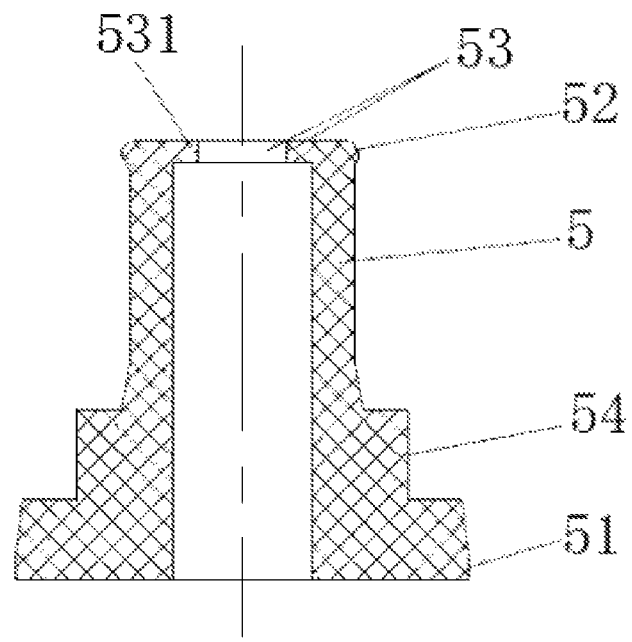
FIG. 6 is a sectional view of a locking body according to one embodiment of the present invention.
Figure 7:
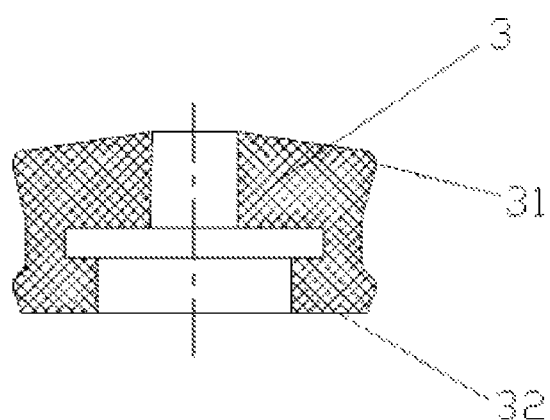
FIG. 7 is a sectional view of a rubber plug according to one embodiment of the present invention.
Figure 8:
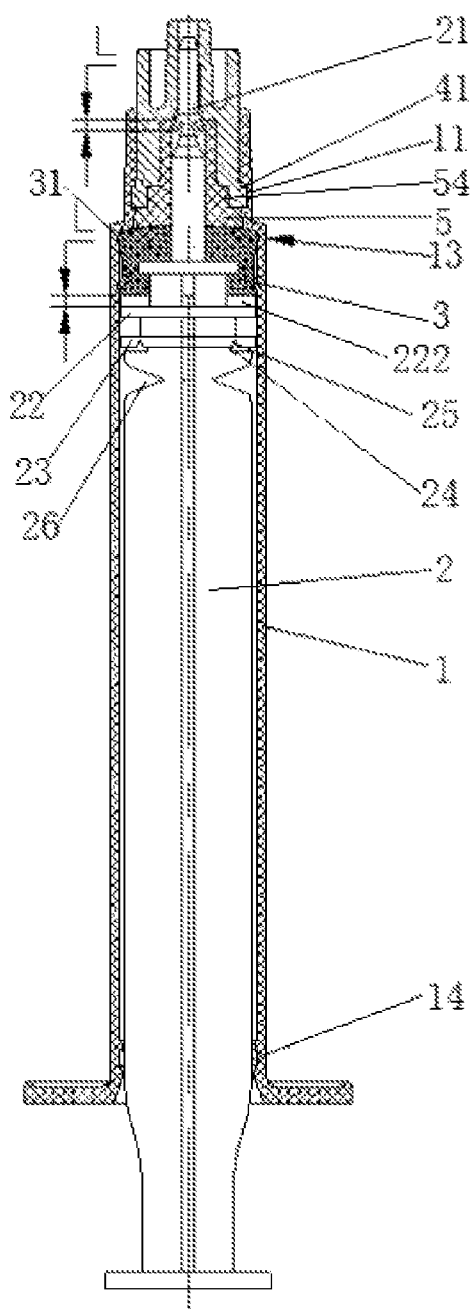
FIG. 8 is a state diagram that a safety mechanism is not activated after injection according to one embodiment of the present invention.
Figure 9:
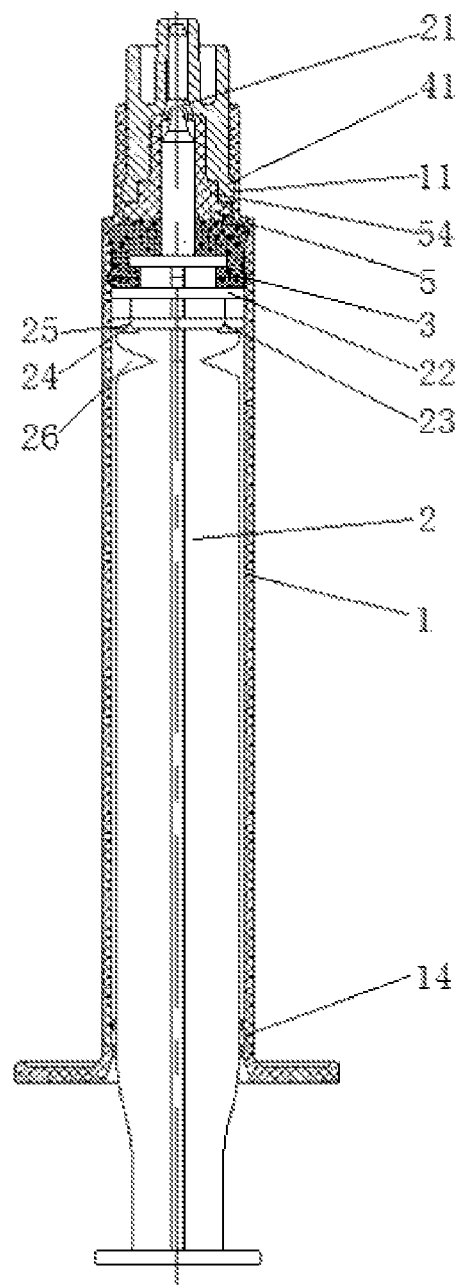
FIG. 9 is a state diagram that the safety mechanism is activated of the present invention.
Figure 10:
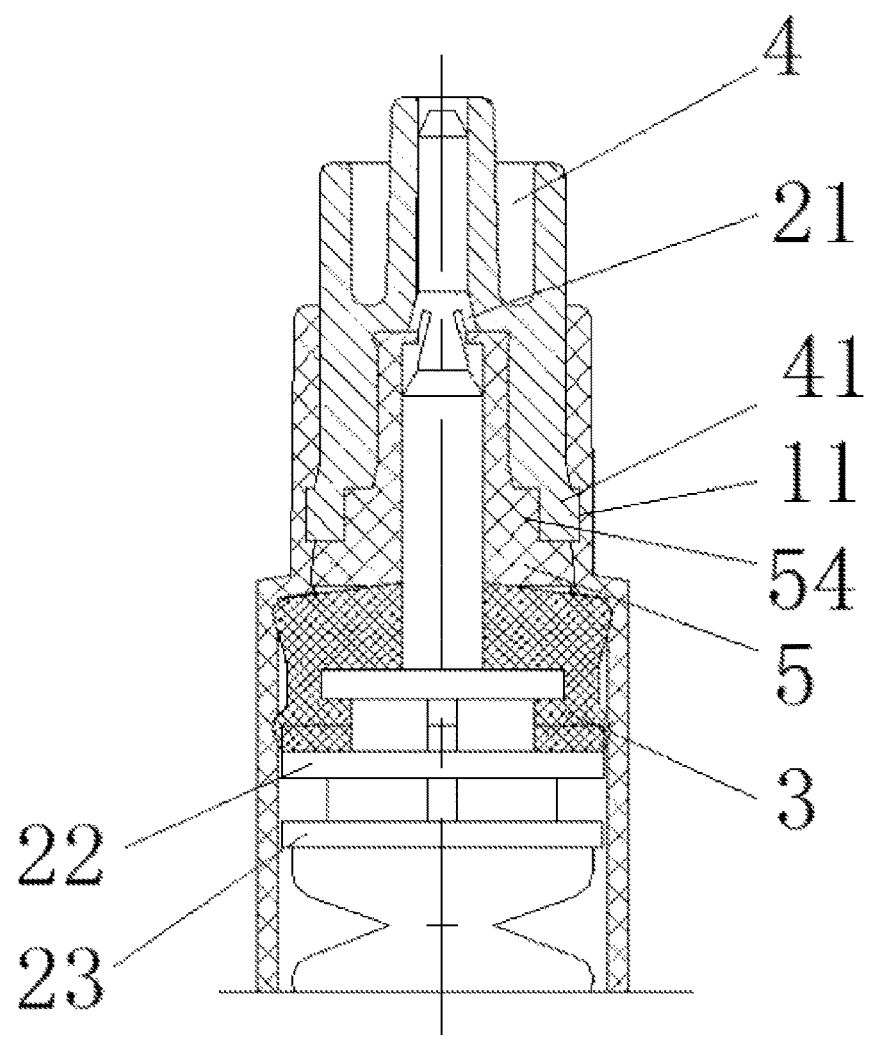
FIG. 10 is a stage diagram that activating ribs are wedged into the rubber plug when the safety mechanism is activated according to one embodiment of the present invention.
Figure 11:
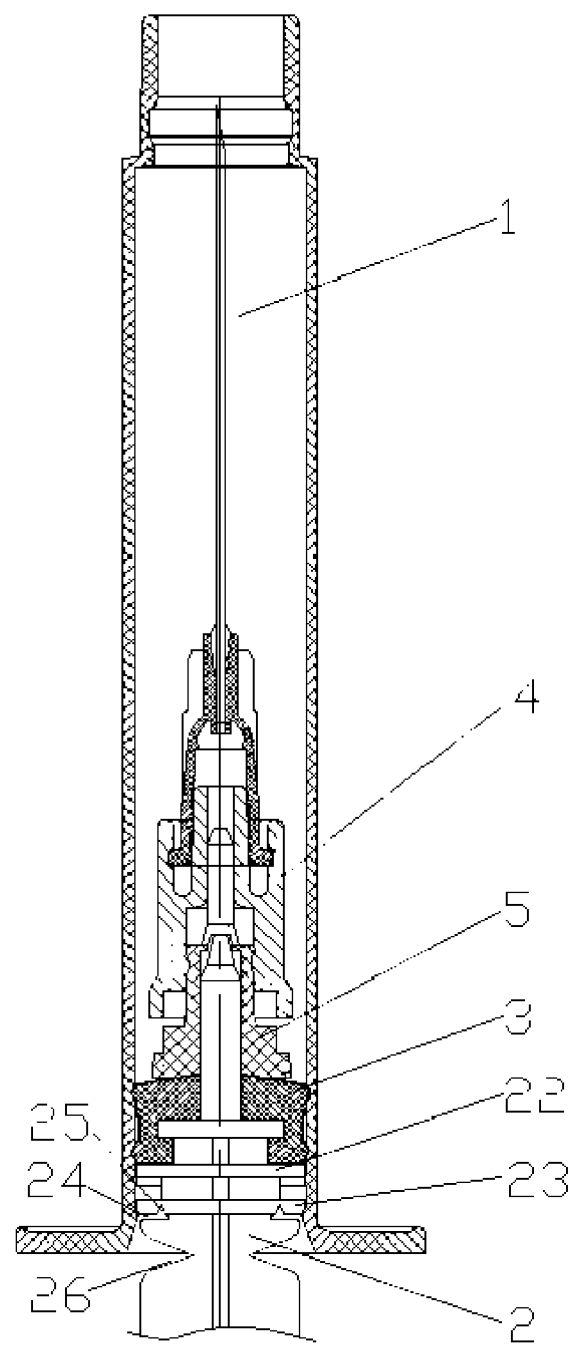
FIG. 11 is a state diagram that a needle is pulled back into the barrel after use of the syringe of the present invention.
Figure 12:
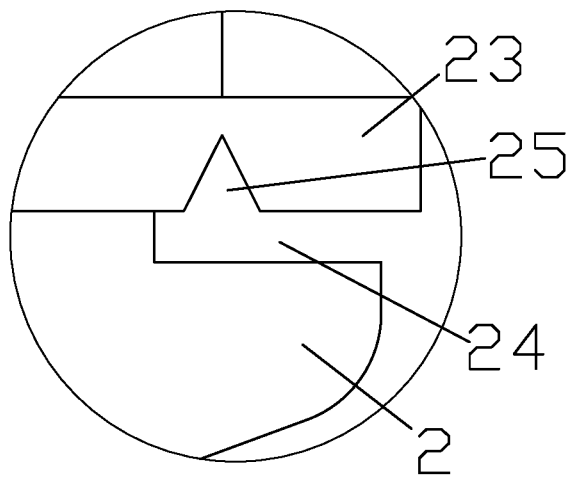
FIG. 12 is an enlarged view of an A portion in FIG. 1.
Figure 13:
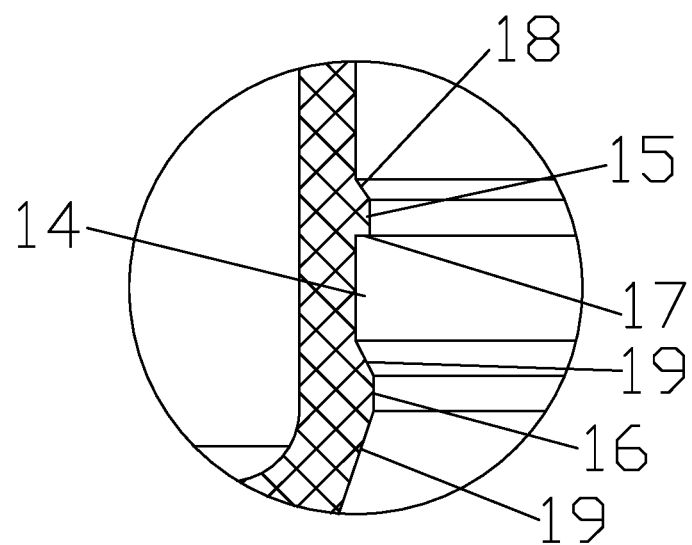
FIG. 13 is an enlarged view of a B portion in FIG. 2.
Figure 14:
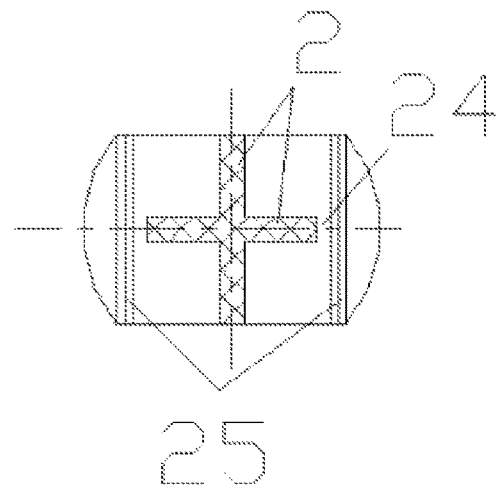
FIG. 14 is a D-D sectional view of the plunger of the present invention.

Referring to FIGS. 1 and 6, the locking body 5 is made of a polymer material with elasticity. The polymer material is thermal plastic elastomer, natural rubber or synthetic rubber.

Referring to FIGS. 1-14, the inner side of the barrel has a front convex ring 15 and a back convex ring 16 which are annularly convex, the front convex ring 15 and the back convex ring 16 are axially arranged along the barrel 1 and the clamping slot 14 is formed between the front convex ring 15 and the back convex ring 16.

Two sides of the front convex ring 15 are of a clamping surface 17 and a guiding surface 18 respectively, the clamping surface 17 faces the back end of the barrel 1 and is vertical to the inner side of the barrel 1, the guiding surface 18 faces the front end of the barrel 1 and is inclined relative to the inner side of the barrel 1, and two sides of the back convex ring 16 are both inclined guiding in surfaces 19.

The clamping disc comprises a front clamping disc 22 and a back clamping disc 23, which are axially arranged along the plunger 2, the outer diameters of the front clamping disc 22 and the back clamping disc 23 are both larger than the inner diameters of the front convex ring 15 and the back convex ring 16, the avoiding seams 24 are adjacent to the back clamping disc 23, and the outer diameters of the front clamping disc 22 and the back clamping disc 23 are both smaller than the inner diameter of the barrel 1. In the present embodiment, the position of the back clamping disc 23 close to the avoiding seams 24 has an inclined chamfer (not shown in the drawings).

The section of the plunger 2 along its radial direction is cross-shaped, each side of the plunger 2 has one avoiding seam 24, and the lower surface of the back clamping disc 23 is provided with a folded line slot 25. The section of the folded line slot 25 in the present embodiment is preferably triangular, and the folded line slot 25 facilitates the bending of the back clamping disc 23 to the avoiding seam 24 during mounting, thus it is favorable for mounting the back clamping disc 23 and the clamping slot 14.

Each side of the plunger 2 is provided with a breaking port 26 for breaking the plunger 2.

During mounting, the plunger 2 is mounted into the barrel 1 by a machine, due to large assembly force of the machine, the force applied to the plunger 2 by the machine makes the front clamping disc 22 and the back clamping disc 23 overcome the stopping action of the front convex ring 15 and the back convex ring 16 to be smoothly mounted, and meanwhile, the folded line slot 25 is arranged to further make the back clamping disc 23 overcome the stopping action of the front convex ring 15 and the back convex ring 16 to be smoothly mounted.

After the syringe is used, an operator pulls the plunger 2 toward the outer end of the barrel 1 by labor, since the side surface of the front convex ring 15 facing the front end of the barrel 1 is the guiding surface 18, when the plunger 2 moves outwards, the chamfer of the back clamping disc 23 close to the avoiding seam 24 moves along the guiding surface 18, the folded line slot 25 causes the back clamping disc 23 to be slightly bent along the folded line slot 25, such that the back clamping disc 23 on the plunger 2 retracts back into the clamping slot 14 and the syringe is in a unusable state.

When the plunger 2 is pushed to the barrel 1 by labor, due to the existence of the front convex ring 15 and the clamping surface 17, one side of the back clamping disc 23 leans against the clamping surface 17 when stressed and is deformed, the folded line slot 25 of the back clamping disc 23 is bent backwards and leans against the side part of the avoiding seams 24, the deformation quantity of the back clamping disc 23 reaches a maximal value but the back clamping disc 23 still abuts against the clamping surface 17 of the front convex ring 15, such that the plunger 2 cannot be easily loaded into the barrel 1 by an external force and the aim that the syringe cannot be reused after disposable use.

Meanwhile, when the back clamping disc 23 on the plunger 2 retracts back into the clamping slot 14, the user can break the plunger 2 from the breaking port 26 by labor, thereby reducing the space occupation of a waste syringe in transportation and avoiding reuse of the syringe after disposable use.

Referring to FIGS. 1-3 and 6-8, when the zero line 13 of the barrel 1 and a front sealing line 31 of the rubber plug 3 are coincided, a gap with an activating displacement L is reserved between the front end surface 221 of the front clamping disc 22 of the plunger 2 and the bottom end surface 32 of the rubber plug 3; another gap with an activating displacement L is reserved between the bottom end surface 221 of the pull pawl 21 of the plunger 2 and the front end surface 531 of the clamping ring 53.

Referring to FIGS. 1, 2, 5 and 6, the clamping slot 11 of the barrel 1 is an annular groove and is meshed with the annular clamping pawls 41 of the needle connector 4, and after the checking ring 54 of the locking body 5 is plugged into the inner cavity of the annular clamping pawls 41, the needle connector 4 is firmly fixed on the barrel 1; and after the checking ring 54 of the locking body 5 is moved from the inner cavity 411 of the annular clamping pawls 41, the annular clamping pawls 41 can be folded so as to smoothly enter the inner cavity of the barrel 1.

Referring to FIGS. 1, 2, 5 and 6, the large sealing ring 12 of the barrel 1 and the sealing disc 51 of the locking body 5 constitute the sealing structure A by interference fit, the sealing ring 52 at the front end of the locking body 5 and the inner sealing ring 42 of the needle connector 4 are matched to constitute the sealing structure B, and the sealing structures A and B keep the airtightness of the barrel 1.

Figure 3:
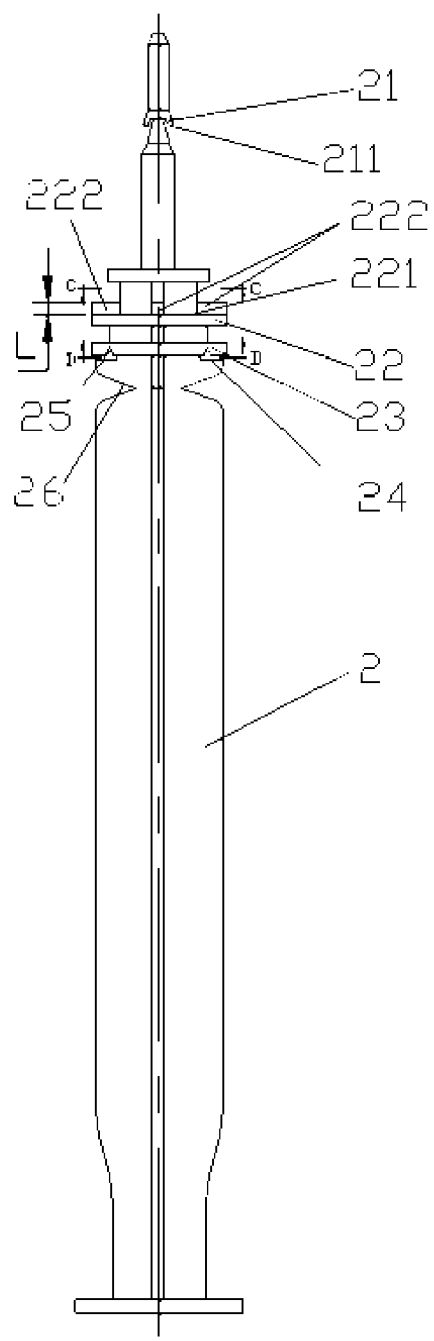
FIG. 3 is a diagram of a plunger according to one embodiment of the present invention.

Referring to FIGS. 1, 3 and 6, the pull pawl 21 of the plunger 2 is capable of being opened and closed, when opened, the outer diameter of the pull pawl 21 is larger than the inner diameter of the clamping ring 53 of the locking body 5, and after penetrating through the clamping ring 53, the pull pawl 21 is opened to be clamped on the front end surface 531 of the clamping ring 53; at this point, the plunger 2 can drag the locking body 5 to move into the barrel 1.

Referring to FIGS. 1, 3, 4 and 7, two or more activating ribs 222 are uniformly distributed on the front end surface 221 of the front clamping disc 22 of the plunger 2 and the height of the activating ribs 222 is equal to the reserved activating displacement L; and when the plunger 2 moves forward, the activating ribs 222 support the bottom end surface 32 of the rubber plug 3 to inject.

Figure 4:
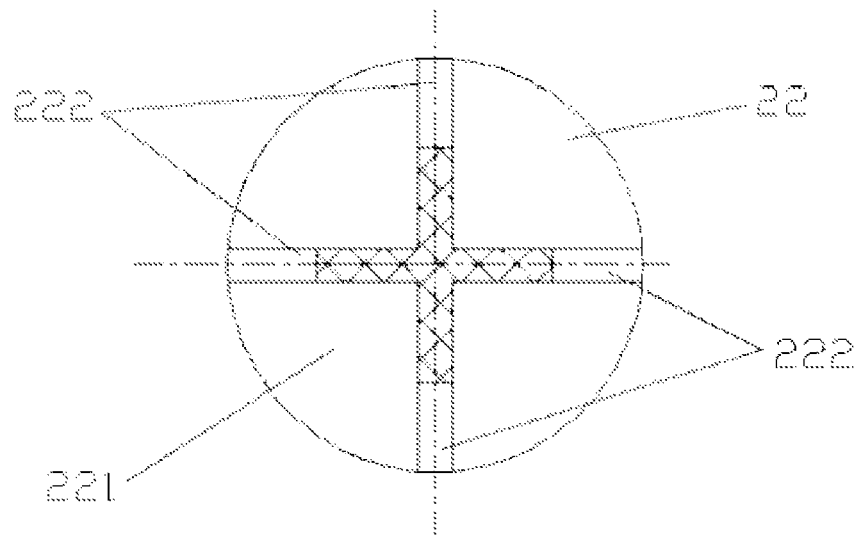
FIG. 4 is a C-C sectional view of a plunger according to one embodiment of the present invention.

FIG. 4 shows four activating ribs 222, the sectional shape of the activating ribs 222 can be round, rectangular or triangular, and is rectangular in the present embodiment; a projection total area of the activating ribs 222 on the front clamping disc 22 is smaller than the area of the front clamping disc 22, and an area ratio in the present embodiment is 1:10 and 1:30 and optimally 1:15.

Referring to FIGS. 1, 3, 4, 6, 7 and 9, the activating ribs 222 are capable of moving to the bottom end surface 32 of the rubber plug 3 when the plunger 2 is subjected to an axial activating force and is wedged into the rubber plug 3 to move by certain displacement L, the pull pawl 21 penetrates through the clamping ring 53 of the locking body 5 and is then opened to be clamped on the front end surface 531 of the clamping ring 53, at this point, the plunger 2 and the locking body 5 are clamped into a whole completely, and the safety mechanism of the safety syringe is activated.

Figure 5:
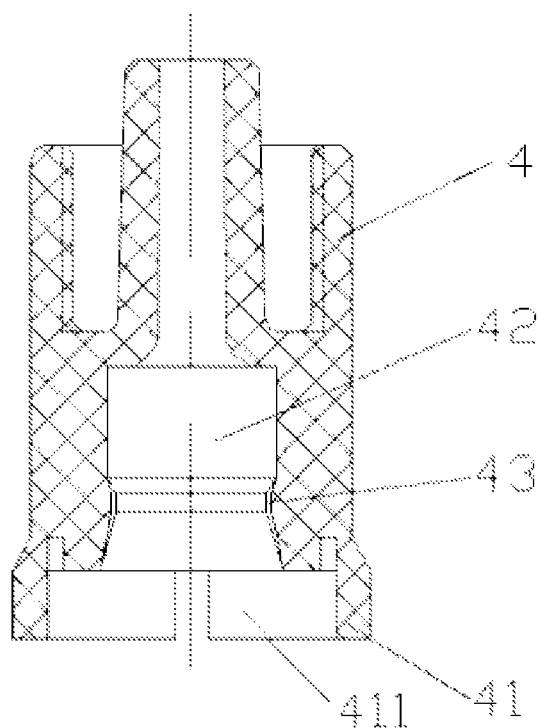
FIG. 5 is a sectional view of a needle connector according to one embodiment of the present invention.

Referring to FIGS. 1 and 5, the annular clamping pawls 41 of the needle connector 4 are radially uniformly distributed and have a number of more than two, and the number of the clamping pawls 41 in the present embodiment is preferably 4.

Referring to FIGS. 1, 2, 5 and 6, the annular clamping pawls 41 on the needle connector 4 are meshed with the clamping slot 11 at the front end of the barrel 1, when the checking ring 54 of the locking body 5 is plugged into the inner cavity 411 of the clamping pawls 41, the clamping pawls 41 are jacked to not retract to the center, and the needle connector 4 is firmly fixed on the barrel 1.

Referring to FIGS. 1-3, 5 and 6, the large sealing ring 12 of the barrel 1 and the sealing disc 51 of the locking body 5 constitute the sealing structure A by interference fit, and the sealing ring 52 of the locking body 5 and the sealing ring 42 of the needle connector 4 are matched to constitute the sealing structure B, and these two sealing structures can solve the airtightness problem of the barrel 1 such that the syringe is not leaked in use. Since the locking body 5 achieves the three actions of fixing the needle connector 4, constituting the two sealing structures A and B and dragging to retract the needle connector, and one part has three actions, thus reducing the number of parts. Further since the locking body 5 is made of the polymer material with elasticity, the constituted sealing structures are very reliable.

Referring to FIGS. 1-3, 5-7 and 9-11, when the plunger 2 drags the rubber plug 3 till the front sealing line 31 of the rubber plug 3 and the zero line 13 of the barrel are coincided, it means that liquid in the barrel 1 is totally injected, at this point, the pull pawl 21 of the plunger 2 is away from the front end of the clamping ring 53 of the locking body 5 by a distance L, the plunger 2 and the locking body 5 are not locked into a whole yet, the locking body 5 is impossible to be hooked to retract, and the syringe cannot be failed due to retracting of the plunger 2 and can finish operations such as air exhausting and multi-injection and the like. When deciding to not use the syringe any more after reinjection, medical staff can apply a force to the plunger 2 in the axial direction, the activating ribs 222 on the front clamping disc 22 of the plunger 2 will be wedged into the rubber plug 3 and move forward by the distance L, then the pull pawl 21 of the plunger 2 penetrates through the clamping ring 51 of the locking body 5 to reach the front end surface of the clamping ring 5, since the outer diameter of the pull pawl 21 is larger than the inner diameter of the clamping ring 53 of the locking body 5, the pull pawl 21 connects the plunger 2 and the locking body 5 into a whole to retract the plunger 2 back into the barrel 1, the plunger 2 drives the locking body 5 to also retract into the barrel 1 to relieve the constraint to the clamping pawls 41 of the needle connector 4, the plunger 2 is continued to pull to retract the locking body 5 continuously, when the sealing ring 52 of the locking body 5 hooks the pullback ring 43 of the needle connector 4, the needle connector 4 without constraint is also pulled into the barrel 1, the needle connected to the needle connector 4 is pulled back into the barrel to be shielded, and thus the needle polluted by patient's blood will not cause harm.

When the safety syringe is used, the syringe is in a state as shown in FIG. 1, and the needle connector 4 is provided with an injection needle (not shown in the drawing). The plunger 2 is pulled back to finish liquid discharging and air exhausting, the plunger 2 is pushed to the bottom to finish the injection (FIG. 8), since the pull pawl 21 of the plunger 2 does not penetrate through the locking body 5 and is clamped at the outside of the locking body 5. The plunger 2 can also be dragged back for injection the next time. Also the injection needle can be pulled out of a human body, a force is applied to the plunger 2 in the axial direction to move the plunger 2 forwards by a distance L, in the meantime, the safety mechanism is activated (FIG. 9), the plunger 2 and the locking body 5 are locked into a whole, and the pull rod 2 is continued to move to pull and shield the needle connector 4 together with the needle thereon into the barrel 1 as the state shown in FIG. 11.

If not activated, the safety syringe is continued to be used; and in vitro activating can avoid the pain of a patient caused by swing of the needle during activating.

Thus, the safety syringe meets the requirements of the International Standard ISO7886-4, the safety device can be selectively activated, the polluted needle can be retracted back into the barrel 1 to be totally shielded, and needle puncture harm is avoided. Since the one part, i.e., locking body 5 achieves three actions of fixing the needle connector 4, constituting the reliable sealing structures with corresponding parts of the needle connector 4 and the barrel 1 respectively and dragging the needle on the needle connector 4 back to retract into the barrel 1, three actions are realized by one part, the integral structure is simplified and the production cost is reduced. The sealing structures are formed without using the small-sized O-shaped rings, thus mechanical production is easy to realize.

Embodiments of Activating Ribs

The selectively activated retractable safety syringe of 5 ml is taken as an example, 4 activating ribs are arranged on the front clamping disc of the plunger, and have a cuboid shape (referring to FIG. 4). The size of each activating rib is: length 2 mm and height 1 mm.

Embodiment 1

Figure 15:
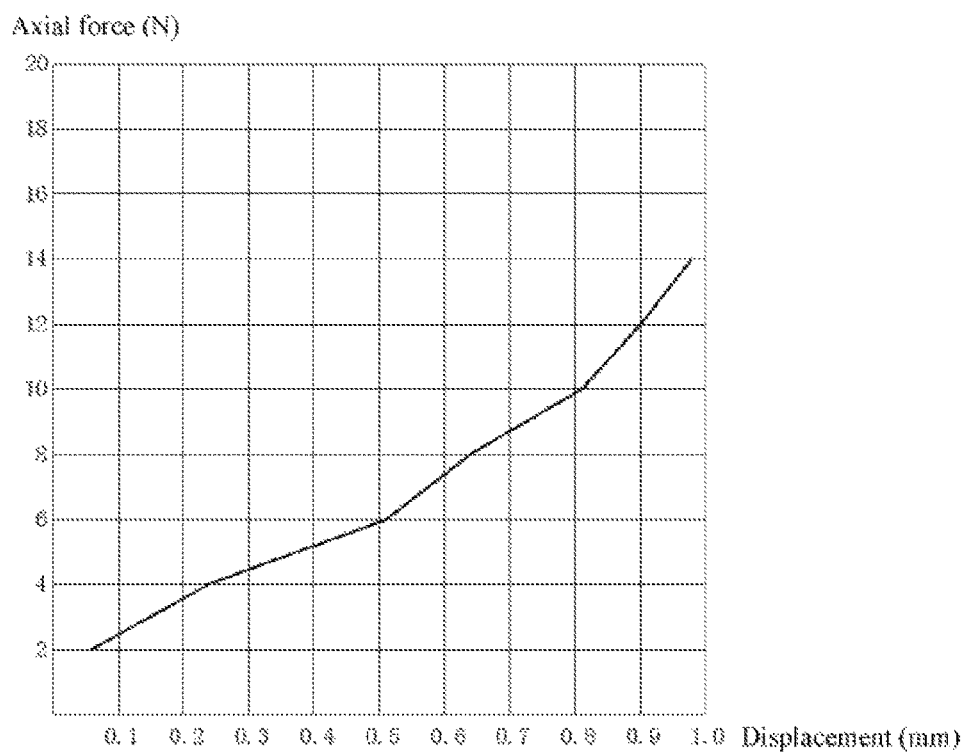
FIG. 15 is a relational graph between a displacement and an axial force when the activating ribs are 0.5 mm wide according to one embodiment of the present invention.

Table 1 is a relationship between a displacement and an axial activating force when the activating ribs are 0.5 mm wide, while a curve plot is shown in FIG. 15.

TABLE 1 a relationship between a displacement and an axial activating force when the activating ribs are 0.5 mm wide

| Number | Activating rib width (mm) | Displacement (mm) | Axial force (N) |
| --- | --- | --- | --- |
| 1 | 0.5 | 0.06 | 2 |
| 2 | 0.5 | 0.24 | 4 |
| 3 | 0.5 | 0.51 | 6 |
| 4 | 0.5 | 0.64 | 8 |
| 5 | 0.5 | 0.81 | 10 |
| 6 | 0.5 | 0.90 | 12 |
| 7 | 0.5 | 0.98 | 14 |

Embodiment 2

Figure 16:
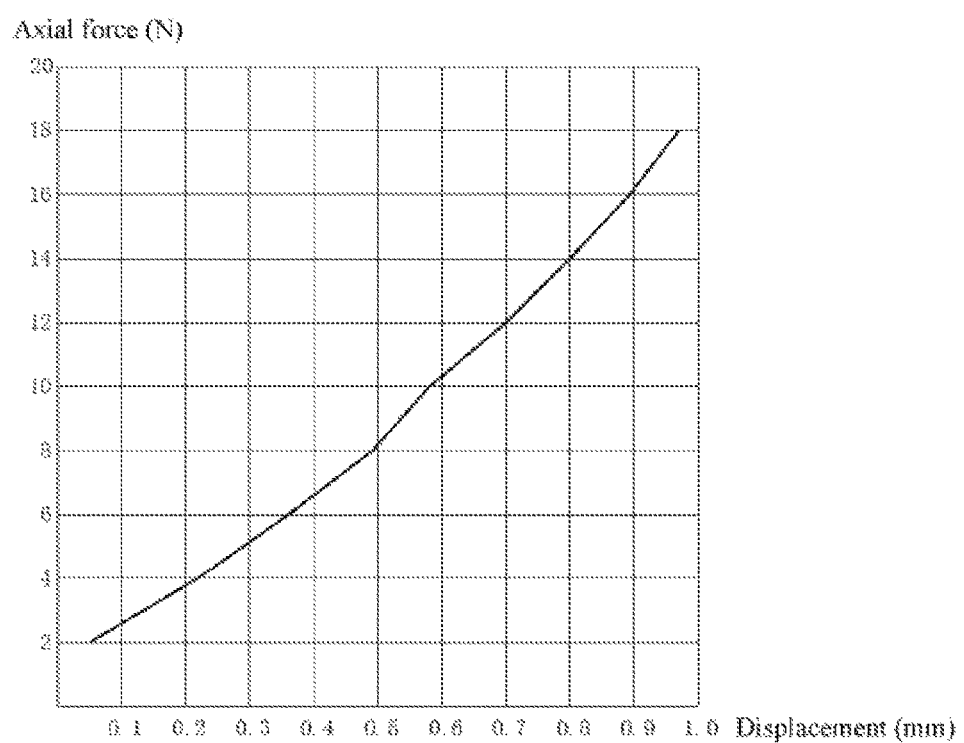
FIG. 16 is a relational graph between a displacement and an axial force when the activating ribs are 0.8 mm wide according to one embodiment of the present invention.

Table 2 is a relationship between a displacement and an axial activating force when the activating ribs are 0.8 mm wide. The curve plot is shown in FIG. 16.

TABLE 2 a relationship between a displacement and an axial activating force when the activating ribs are 0.8 mm wide

| Number | Activating rib width (mm) | Displacement (mm) | Axial force (N) |
| --- | --- | --- | --- |
| 1 | 0.8 | 0.05 | 2 |
| 2 | 0.8 | 0.22 | 4 |
| 3 | 0.8 | 0.36 | 6 |
| 4 | 0.8 | 0.49 | 8 |
| 5 | 0.8 | 0.58 | 10 |
| 6 | 0.8 | 0.70 | 12 |
| 7 | 0.8 | 0.80 | 14 |

TABLE 2-continued a relationship between a displacement and an axial
activating force when the activating ribs are 0.8 mm wide

| Number | Activating rib width (mm) | Displacement (mm) | Axial force (N) |
|---|---|---|---|
| 8 | 0.8 | 0.89 | 16 |
| 9 | 0.8 | 0.97 | 18 |

Embodiment 3

Figure 17:
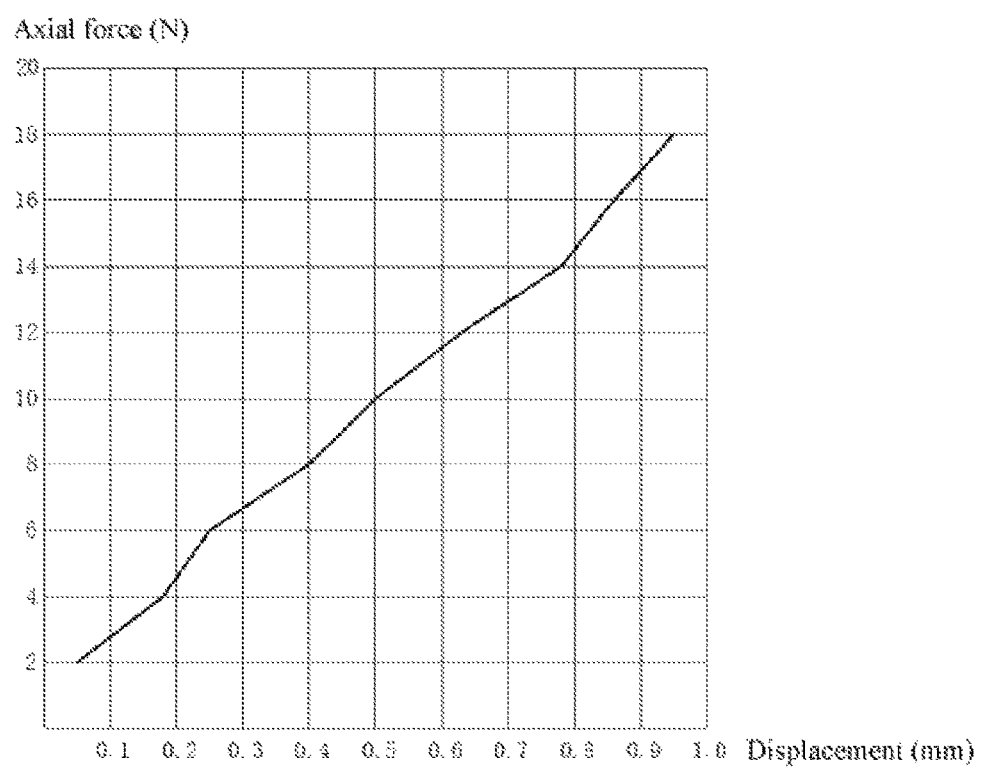
FIG. 17 is a relational graph between a displacement and an axial force when the activating ribs are 1.0 mm wide according to one embodiment of the present invention.

Table 3 is a relationship between a displacement and an axial activating force when the activating ribs are 1 mm wide. The curve plot is shown in FIG. 17.

TABLE 3 a relationship between a displacement and an axial
activating force when the activating ribs are 1 mm wide

| Number | Activating rib width (mm) | Displacement (mm) | Axial force (N) |
|---|---|---|---|
| 1 | 1 | 0.05 | 2 |
| 2 | 1 | 0.18 | 4 |
| 3 | 1 | 0.25 | 6 |
| 4 | 1 | 0.40 | 8 |
| 5 | 1 | 0.50 | 10 |
| 6 | 1 | 0.63 | 12 |
| 7 | 1 | 0.78 | 14 |
| 8 | 1 | 0.86 | 16 |
| 9 | 1 | 0.95 | 18 |

The foregoing description of the exemplary embodiments of the invention has been presented only for the purposes of illustration and description and is not intended to be exhaustive or to limit the invention to the precise forms disclosed. Many modifications and variations are possible in light of the above teaching.

The embodiments were chosen and described in order to explain the principles of the invention and their practical application so as to activate others skilled in the art to utilize the invention and various embodiments and with various modifications as are suited to the particular use contemplated. Alternative embodiments will become apparent to those skilled in the art to which the present invention pertains without departing from its spirit and scope. Accordingly, the scope of the present invention is defined by the appended claims rather than the foregoing description and the exemplary embodiments described therein.

What is claimed is:

1. A safety syringe, comprising:
an annular hollow barrel (1), a plunger (2) capable of sliding in the barrel (1), a rubber plug (3) mounted on the plunger (2), a slidable needle connector (4) mounted at a front end of the barrel (1), and a locking body (5) capable of clamping a needle connector (4) on the barrel (1) and forming a sealing structure together with the barrel (1) and needle connector (4), wherein the locking body (5) is meshed with the plunger (2) and then dragged back into the barrel (1) by the plunger (2), and is made of a polymer material with elasticity,
wherein the front end of the barrel (1) is provided with a clamping slot (11), a large sealing ring (12) and a zero line (13), and an inner side of a back end of the barrel (1) has an annular concave clamping slot (14);
wherein a front end of the plunger (2) is provided with a pull pawl (21) and an annular convex clamping disc, the plunger (2) has avoiding seams (24) adjacent to a clamping disc, an outer diameter of the clamping disc is smaller than an inner diameter of the clamping slot (14) of the barrel (1), the clamping disc has elasticity and is located in the clamping slot (14) when being pushed to be deformed by the plunger (2);
wherein the needle connector (4) is provided with annular clamping pawls (41), an inner sealing ring (42) and a pullback ring (43); and
wherein the locking body (5) is provided with a sealing disc (51), a sealing ring (52), a clamping ring (53) and a checking ring (54), the sealing disc (51) and the large sealing ring (12) of the barrel (1) are matched to constitute a sealing structure A, the sealing ring (52) and the inner sealing ring (42) of the needle connector are matched to constitute a sealing structure B, the sealing ring (52) and the pullback ring (43) of the needle connector are matched to pull the needle connector (4) to retract, the clamping ring (53) and the pull pawl (21) of the plunger (2) are meshed to be dragged by the plunger (2) to retract inwards, and the checking ring (54) is capable of being plugged into the inner cavity (411) of the clamping pawls (41) of the needle connector (4) to fix the clamping pawls (41) in the clamping slot (11) of the barrel (1).

2. The safety syringe according to claim 1, wherein an inner side of the barrel (1) has a front convex ring (15) and a back convex ring (16) which are annularly convex, the front convex ring (15) and the back convex ring (16) are axially arranged along the barrel (1) and the annular concave clamping slot (14) is formed between the front convex ring (15) and the back convex ring (16).

3. The safety syringe according to claim 2, wherein the clamping disc comprises a front clamping disc (22) and a back clamping disc (23), which are axially arranged along the plunger (2), the outer diameters of the front clamping disc (22) and the back clamping disc (23) are both larger than the inner diameters of the front convex ring (15) and the back convex ring (16), and the avoiding seams (24) are adjacent to the back clamping disc (23).

4. The safety syringe according to claim 3, wherein a section of the plunger (2) along its radial direction is cross-shaped, each side of the plunger (2) has one avoiding seam (24), and the lower surface of the back clamping disc (23) is provided with a folded line slot (25).

5. The safety syringe according to claim 4, wherein each side of the plunger (2) is provided with a breaking port (26) for breaking the plunger (2).

6. The safety syringe according to claim 3, wherein when the zero line (13) of the barrel (1) and a front sealing line (31) of the rubber plug (3) are coincided, a gap with an activating displacement L is reserved between a front end surface (221) of the front clamping disc (22) of the plunger (2) and a bottom end surface (32) of the rubber plug (3); another gap with an activating displacement L is reserved between a bottom end surface (221) of the pull pawl (21) of the plunger (2) and front end surface (531) of the clamping ring (53) of the locking body (5).

7. The safety syringe according to claim 1, wherein the clamping slot (11) of the barrel (1) is an annular groove and is meshed with the annular clamping pawls (41) of the needle connector (4), and after the checking ring (54) of the locking body (5) is plugged into the inner cavity of the annular clamping pawls (41), the needle connector (4) is firmly fixed on the barrel (1); and after the checking ring (54) of the locking body (5) is moved from the inner cavity (411) of the annular clamping pawls (41), the annular clamping pawls (41) is capable of being folded so as to smoothly enter the inner cavity of the barrel (1).

8. The safety syringe according to claim 1, wherein the large sealing ring (12) of the barrel (1) and the sealing disc (51) of the locking body (5) constitute the sealing structure A by interference fit, the sealing ring (52) at the front end of the locking body (5) and the inner sealing ring (42) of the needle connector (4) are matched to constitute the sealing structure B, and the sealing structures A and B keep the airtightness of the barrel (1).

9. The safety syringe according to claim 1, wherein the pull pawl (21) of the plunger (2) is capable of being opened and closed, when opened, the outer diameter of the pull pawl (21) is larger than the inner diameter of the clamping ring (53) of the locking body (5), and after penetrating through the clamping ring (53), the pull pawl (21) is opened to be clamped on a front end surface (531) of the clamping ring (53); at this point, the plunger (2) is capable of dragging the locking body (5) to move into the barrel (1).

10. The safety syringe according to claim 6, wherein two or more activating ribs (222) are uniformly distributed on the front end surface (221) of the front clamping disc (22) of the plunger (2) and the height of the activating ribs (222) is equal to the reserved activating displacement L; and when the plunger (2) moves forward, the activating ribs (222) support the bottom end surface (32) of the rubber plug (3) to inject.

11. The safety syringe according to claim 10, wherein a sectional shape of the activating ribs (222) is round, rectangular or triangular.

12. The safety syringe according to claim 10, wherein a projection total area of the activating ribs (222) on the front clamping disc (22) is smaller than the area of the front clamping disc (22).

13. The safety syringe according to claim 10, wherein the activating ribs (222) are capable of moving to the bottom end surface (32) of the rubber plug (3) when the plunger (2) is subjected to an axial activating force and is wedged into the rubber plug (3) to move by certain displacement L, the pull pawl (21) penetrates through the clamping ring (53) of the locking body (5) and is then opened to be clamped on the front end surface (531) of the clamping ring (53), at this point, the plunger (2) and the locking body (5) are clamped into a whole completely, and the safety mechanism of the safety syringe is activated.

14. The safety syringe according to claim 1, wherein the annular clamping pawls (41) of the needle connector (4) are radially uniformly distributed and have a number of more than two.

15. The safety syringe according to claim 4, wherein the clamping slot (11) of the barrel (1) is an annular groove and is meshed with the annular clamping pawls (41) of the needle connector (4), and after the checking ring (54) of the locking body (5) is plugged into the inner cavity of the annular clamping pawls (41), the needle connector (4) is firmly fixed on the barrel (1); and after the checking ring (54) of the locking body (5) is moved from the inner cavity (411) of the annular clamping pawls (41), the annular clamping pawls (41) is capable of being folded so as to smoothly enter the inner cavity of the barrel (1).

16. The safety syringe according to claim 12, wherein a sectional shape of the activating ribs (222) is round, rectangular or triangular.

17. The safety syringe according to claim 10, wherein the activating ribs (222) are capable of moving to the bottom end surface (32) of the rubber plug (3) when the plunger (2) is subjected to an axial activating force and is wedged into the rubber plug (3) to move by certain displacement L, the pull pawl (21) penetrates through the clamping ring (53) of the locking body (5) and is then opened to be clamped on the front end surface (531) of the clamping ring (53), at this point, the plunger (2) and the locking body (5) are clamped into a whole completely, and the safety mechanism of the safety syringe is activated.

\* \* \* \* \*